US012753150B2

(12) United States Patent
Min et al.

(10) Patent No.: US 12,753,150 B2
(45) Date of Patent: Oct. 6, 2026

(54) METHOD FOR PREPARING ISOCYANATE COMPOUND

(71) Applicant: Hanwha Solutions Corporation, Seoul (KR)

(72) Inventors: Ju Won Min, Daejeon (KR); Hyun Cheol Ryu, Daejeon (KR); Keedo Han, Daejeon (KR)

(73) Assignee: Hanwha Solutions Corporation, Seoul (KR)

( * ) Notice: Subject to any disclaimer, the term of this patent is extended or adjusted under 35 U.S.C. 154(b) by 620 days.

(21) Appl. No.: 18/259,802

(22) PCT Filed: Dec. 30, 2021

(86) PCT No.: PCT/KR2021/020332
§ 371 (c)(1),
(2) Date: Jun. 29, 2023

(87) PCT Pub. No.: WO2022/146092
PCT Pub. Date: Jul. 7, 2022

(65) Prior Publication Data
US 2024/0067601 A1 Feb. 29, 2024

(30) Foreign Application Priority Data
Dec. 30, 2020 (KR) ........................ 10-2020-0187828

(51) Int. Cl.
*C07C 263/10* (2006.01)
*C07C 263/20* (2006.01)

(52) U.S. Cl.
CPC .......... *C07C 263/10* (2013.01); *C07C 263/20* (2013.01)

(58) Field of Classification Search
CPC ... C07C 263/10; C07C 263/20; C07C 263/16; C07C 265/14
See application file for complete search history.

(56) References Cited

U.S. PATENT DOCUMENTS 7,118,653 B2 10/2006 Brady
7,264,696 B2 * 9/2007 Kaibel .................. B01D 3/141 203/99
10,858,311 B2 * 12/2020 Taube .................. C07C 263/10
2006/0089507 A1 4/2006 Sohn
2020/0190021 A1 6/2020 Zechlin

FOREIGN PATENT DOCUMENTS

CN 101827812 A 9/2010
CN 103086841 A 5/2013
JP 2004-155760 A 6/2004
JP 2009-120528 A 6/2009
(Continued)

OTHER PUBLICATIONS

International Search Report dated Apr. 11, 2022.

*Primary Examiner* — Deborah D Carr
(74) *Attorney, Agent, or Firm* — Harvest IP Law, LLP

(57) ABSTRACT

The present invention relates to a method for preparing an isocyanate compound. According to the present invention, provided is a method for preparing an isocyanate compound that can increase energy efficiency while minimizing thermal denaturation of a reaction product and formation of by-products during the preparation of an isocyanate compound using phosgene.

11 Claims, 2 Drawing Sheets

(56) References Cited

FOREIGN PATENT DOCUMENTS

| | | | |
|---|---|---|---|
| JP | 2018-533475 | A | 11/2018 |
| JP | 2020-502209 | A | 1/2020 |
| JP | 2020-503325 | A | 1/2020 |
| JP | 2020-533393 | A | 11/2020 |
| KR | 20040035567 | A | 4/2004 |
| KR | 20050089050 | A | 9/2005 |
| KR | 100984426 | B1 | 9/2010 |
| KR | 100996480 | B1 | 11/2010 |
| KR | 20110081239 | A | 7/2011 |
| KR | 101652544 | B1 | 8/2016 |
| KR | 20180069710 | A | 6/2018 |
| KR | 20190142642 | A | 12/2019 |

* cited by examiner

【FIG.1】
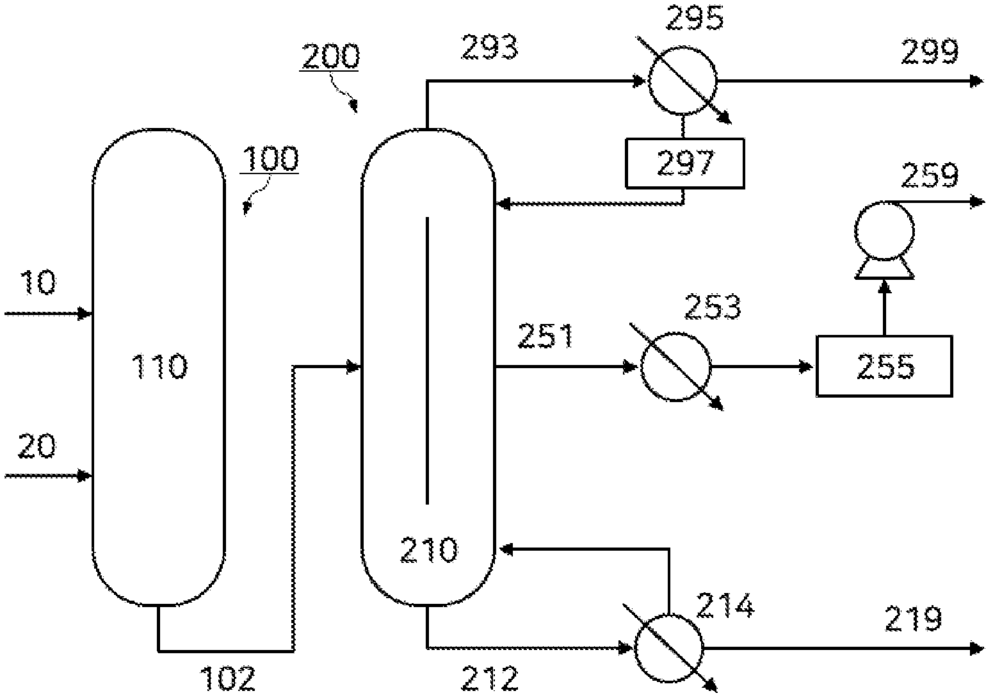

【FIG.2(a)】
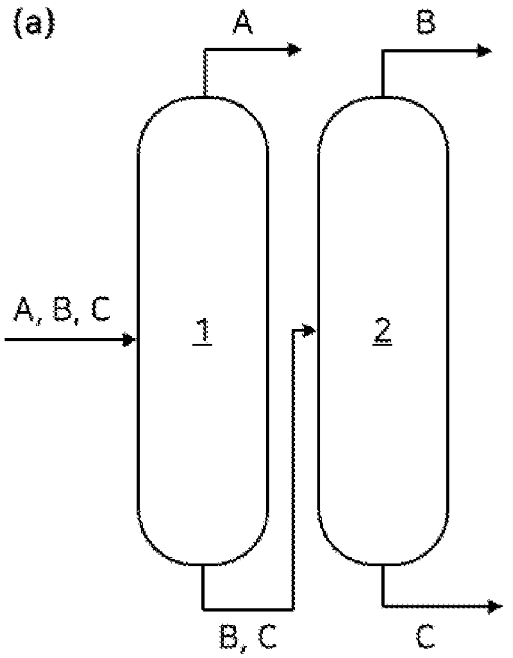
【FIG.2(b)】
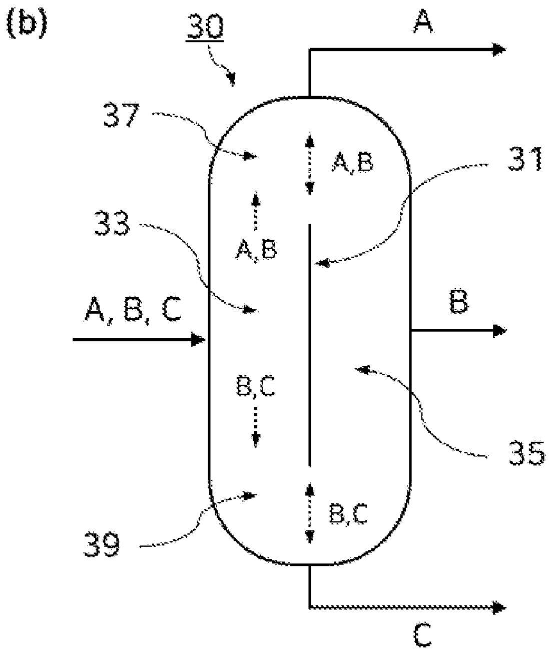

METHOD FOR PREPARING ISOCYANATE COMPOUND

CROSS REFERENCE TO RELATED APPLICATION(S)

This application is a National Stage of International Application No. PCT/KR2021/020332 filed on Dec. 30, 2021, claiming priority based on Korean Patent Application No. 10-2020-0187828 filed Dec. 30, 2020, the disclosures of which are incorporated herein by reference in their entireties.

TECHNICAL FIELD

The present invention relates to a method for preparing an isocyanate compound.

BACKGROUND ART

Although xylylene diisocyanate (hereinafter, referred to as XDI) contains an aromatic ring in its molecule, it is classified into aliphatic isocyanate. XDI is a compound very useful for raw materials such as polyurethane-based materials, polyurea-based materials, or polyisocyanurate-based materials in the fields of chemical industry, resin industry, and paint industry.

Commonly, when synthesizing isocyanate compound, many side reactions are generated, and thus, it is prepared by a method of reacting with anhydrous hydrochloric acid or carbonic acid to form a salt of amine compound and reacting it with phosgene.

As an example, XDI is prepared by reacting xylylene diamine (hereinafter referred to as XDA) with anhydrous hydrochloric acid to form an amine-hydrochloride salt, and then reacting it with phosgene. More specifically, in the prior art, an isocyanate compound such as XDI was prepared by reacting a liquid raw amine, such as XDA-containing solution, with anhydrous hydrochloric acid to form XDA-HCl hydrochloride, heating it to a high temperature of at least 100° C. or more, and then charging gas phase phosgene to progress a gas-liquid reaction.

The reaction of forming the isocyanate compound is a representative endothermic reaction, continuous heating and maintenance of a high temperature are required during the reaction so as to increase the yield.

By the way, since isocyanate compound such as XDI generally has high reactivity of the amino group, many side reactions are generated during the phosgenation reaction, and the by-products formed through the side reactions have an influence on a process in which isocyanate compounds are applied as raw materials (for example, a process for producing a polyurethane resin), thereby causing deterioration in resin quality.

As explained above, due the need to maintain a high temperature during the preparation process of isocyanate compound, and the high reactivity of the prepared isocyanate compound, such as XDI, there is a growing concern about the formation of by-products or the occurrence of side reactions by the thermal denaturation of products, and thus, high load has been frequently generated even in the purification process.

Due to such problems, various attempts have been made in the past to suppress side reactions or by-product generations during the preparation of isocyanate compound, but effective technology has not yet been developed.

DETAILED DESCRIPTION OF THE INVENTION

Technical Problem

It is an object of the present invention to provide a method for preparing an isocyanate compound that can increase energy efficiency while minimizing thermal denaturation of a reaction product and formation of by-products during the preparation of an isocyanate compound using phosgene.

Technical Solution

According to one embodiment of the present invention, there is provided a method for preparing isocyanate compound, comprising:

a reaction step of reacting a salt of amine compound with phosgene in the presence of a solvent to obtain a reaction product containing an isocyanate compound, the solvent and unreacted phosgene, and a distillation step of distilling the reaction product in a dividing-wall distillation column, so that a stream containing the unreacted phosgene is obtained from the top of the dividing-wall distillation column, a stream containing the isocyanate compound is obtained from the bottom of the dividing-wall distillation column, and a stream containing the solvent is obtained from a side stream draw of the dividing-wall distillation column, wherein the distillation step is progressed so that the temperature at the bottom of the dividing-wall distillation column is 165° C. or less.

Now, a method for preparing an isocyanate compound according to one embodiment of the present invention will be described.

Unless defined otherwise, all technical and scientific terms used herein have the same meaning as commonly understood by one of ordinary skill in the art to which this invention belongs. The terms used herein are for the purpose of describing specific embodiments only and is not intended to limit the scope of the invention.

The singular forms "a," "an" and "the" used herein are intended to include plural forms, unless the context clearly indicates otherwise.

It should be understood that the terms "comprise," "include", "have", etc. are used herein to specify the presence of stated feature, region, integer, step, action, element and/or component, but do not preclude the presence or addition of one or more other feature, region, integer, step, action, element, component and/or group.

While the present invention can be modified in various ways and take on various alternative forms, specific embodiments thereof are illustrated and described in detail below. However, it should be understood that there is no intent to limit the present invention to the particular forms disclosed, but on the contrary, the present invention covers all modifications, equivalents, and alternatives falling within the spirit and scope of the present invention.

In describing a position relationship, for example, when the position relationship is described as 'upon~', 'above~', 'below~', and 'next to~', one or more portions may be arranged between two other portions unless 'just' or 'direct' is used.

In describing a time relationship, for example, when the temporal order is described as 'after~', 'subsequent~', 'next~', and 'before~', a case which is not continuous may be included unless 'just' or 'direct' is used.

As used herein, the term "low boiling material" means a material having a boiling point lower than that of the isocyanate compound which is a target product according to the present invention, and the term "high boiling material" means a material having a boiling point higher than that of the isocyanate compound, which is a target product according to the present invention.

As used herein, the term "bottom" of the distillation column means an outlet through which the lower discharged products of the distillation column are discharged to the outside of the distillation column, the term "top" of the distillation column means an outlet through which the upper discharged products of the distillation column are discharged to the outside of the distillation column.

According to one embodiment of the present invention, there is provided a method for preparing isocyanate compound, comprising:

a reaction step of reacting a salt of amine compound with phosgene in the presence of a solvent to obtain a reaction product containing an isocyanate compound, the solvent and unreacted phosgene, and a distillation step of distilling the reaction product in a dividing-wall distillation column, so that a stream containing the unreacted phosgene is obtained from the top of the dividing-wall distillation column, a stream containing the isocyanate compound is obtained from the bottom of the dividing-wall distillation column, and a stream containing the solvent is obtained from a side stream draw of the dividing-wall distillation column, wherein the distillation step is progressed so that the temperature at the bottom of the dividing-wall distillation column is 165° C. or less.

High purity is required to use isocyanate compounds as raw materials for fine chemical products including optical materials.

However, generally, when synthesizing an isocyanate compound including XDI, there is a problem that many side reactions occur, and the purity of the isocyanate compound is lowered due to reaction between reaction products and thermal denaturation.

In one example, aliphatic diisocyanate can be prepared by reacting an aliphatic diamine with phosgene. At this time, a side reaction occurs, and as a side reaction product, for example, a monoisocyanate such as (chloromethyl)benzyl isocyanate is produced. It is known that the occurrence of such side reactions and the formation of by-products are caused by the need to maintain a high temperature during the preparation process of aliphatic diisocyanate and the high reactivity of the prepared aliphatic diisocyanate such as XDI. In particular, the final product, aliphatic diisocyanate, causes side reactions when exposed to high temperatures for a certain period of time, or can form high-molecular-weight by-products, such as oligomers or polymers, including dimers or trimers or higher oligomers.

The present inventors have found, as a result of continuous research, that when distilling the reaction product from the phosgenation reaction of an amine compound using a dividing-wall distillation column, energy efficiency can be increased while minimizing thermal denaturation of reaction products and formation of by-products.

Numerous materials such as phosgene as a raw material, a solvent, and low boiling materials and high boiling materials as by-products are mixed in the reaction product. In order to obtain a high-purity isocyanate compound from the reaction product, the same number of evaporators as the components of the impurity to be separated should be continuously arranged. And, when a solvent having a corresponding boiling point between phosgene and an isocyanate compound is used in the phosgenation reaction, remixing with other components takes place within the evaporator until the solvent is removed. By the way, since the solvent accounts for 80% by weight or more of the reaction product, there is a problem that the energy efficiency up to the step of removing the solvent is remarkably lowered.

In the method for preparing an isocyanate compound according to an embodiment of the invention, a dividing-wall distillation column is applied, and thus, the solvent can be obtained from a side stream draw of the dividing-wall distillation column. Thus, no separate evaporator or process for removing the solvent is not required, and process operation burden and energy consumption due to solvent remixing can be reduced.

FIG. 1 schematically shows the process and apparatus used in a method for preparing an isocyanate compound according to an embodiment of the present invention.

Each step that can be included in the method for preparing an isocyanate compound according to an embodiment of the invention will be described below with reference to FIG. 1.

(Reaction Step)

First, a reaction step is progressed in which a salt of amine compound and phosgene are reacted in the presence of a solvent to obtain a reaction product containing an isocyanate compound, the solvent, and unreacted phosgene.

According to one embodiment of the invention, the amine compound is preferably applied as a salt of the amine compound in order to suppress rapid reactions and side reactions between the amine compound and phosgene. For example, the salt of amine compound may be a hydrochloride or carbonic acid salt of the amine compound.

The salt of the amine compound may be prepared by reacting an amine compound with anhydrous hydrochloric acid or carbonic acid and performing a neutralization reaction. The neutralization reaction can be progressed at a temperature of 20 to 80° C.

The supply ratio of the anhydrous hydrochloric acid or carbonic acid may be, for example, 2 to 10 moles, 2 to 6 moles, or 2 to 4 moles, based on 1 mole of the amine compound.

Preferably, the amine compound may be a fatty amine having an aliphatic group in its molecule. Specifically, the aliphatic amine may be a chained or cyclic aliphatic amine. More specifically, the aliphatic amine may be a bifunctional or higher chained or cyclic aliphatic amine containing at least two amino groups in its molecule.

For example, the amine compound may be at least one compound selected from the group consisting of hexamethylenediamine, 2,2-dimethylpentanediamine, 2,2,4-trimethylhexanediamine, butenediamine, 1,3-butadiene-1,4-diamine, 2,4,4-trimethylhexamethylenediamine, 1,6,11-undecatriamine, 1,3,6-hexamethylenetriamine, 1,8-diisocyanato-4-(isocyanatomethyl)octane, bis(aminoethyl) carbonate, bis(aminoethyl)ether, xylylenediamine, α,α,α',α'-tetramethylxylylenediamine, bis(aminoethyl)phthalate, bis(aminomethyl)cyclohexane, dicyclohexylmethanediamine, cyclohexanediamine, methylcyclohexanediamine, dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl) tricyclodecane, 4,8-bis(aminomethyl)tricyclodecane, 4,9-bis (aminomethyl)tricyclodecane, bis(aminomethyl)norbornene, and xylylenediamine.

Further, the amine compound may be at least one sulfur-containing aliphatic amine selected from the group consisting of bis(aminomethyl)sulfide, bis(aminoethyl)sulfide, bis (aminopropyl)sulfide, bis(aminohexyl)sulfide, bis (aminomethyl)sulfone, bis(aminomethyl)disulfide, bis (aminoethyl)disulfide, bis(aminopropyl)disulfide, bis (aminomethylthio)methane, bis(aminoethylthio)methane, bis(aminoethylthio)ethane, bis(aminomethylthio)ethane, and 1,5-diamino-2-aminomethyl-3-thiapentane.

Among the above amine compounds, xylylenediamine (XDA) can exhibit superior effects when applied to the method for preparing an isocyanate compound according to one embodiment of the invention. Preferably, the amine compound may be at least one compound selected from the group consisting of m-xylylenediamine, p-xylylenediamine and o-xylylenediamine.

According to an embodiment of the invention, the reaction step is progressed in a gas-liquid-solid three-phase reaction in which a salt of solid-phase amine compound and gas phase phosgene are reacted in the presence of a solvent. Accordingly, rapid reactions can be effectively suppressed, and side reactions and formation of by-products can be minimized.

When the salt of amine compound and phosgene are reacted in the presence of a solvent, phosgene may be charged at a time, or may be charged dividedly. For example, a small amount of phosgene can be primarily charged at a relatively low temperature, and reacted with the salt of amine compound to produce the intermediate. Subsequently, the remaining amount of phosgene can be secondarily charged at a relatively high temperature, and reacted with the intermediate to obtain a reaction solution containing an isocyanate compound. As an example, xylylene diamine and a small amount of phosgene are reacted to produce an intermediate in the form of a carbamoyl salt, to which the remaining amount of phosgene is then charged, and the intermediate in the form of a carbamoyl salt can be reacted with phosgene to form an aliphatic isocyanate such as xylylene diisocyanate.

Through such reaction steps, a time during which the final product isocyanate compound is exposed to high temperature can be minimized. Furthermore, the intermediate is formed at a relatively low temperature, thereby reducing a time during which a high temperature should be maintained in the whole reaction process. In addition, the amount of heat charged to the whole process can be reduced. Further, the high-temperature reaction time of phosgene can be relatively shortened, and the risk of explosive vaporization of phosgene can also be reduced.

The reaction step is progressed in the presence of a solvent containing at least one of an aromatic hydrocarbon-based solvent and an ester-based solvent. The solvent may be selected in consideration of the temperature at which the reaction step is progressed.

The aromatic hydrocarbon-based solvent may be a halogenated aromatic hydrocarbon-based solvent such as monochlorobenzene, 1,2-dichlorobenzene and 1,2,4-trichlorobenzene.

The ester-based solvent may be fatty acid esters such as amyl formate, n-butyl acetate, isobutyl acetate, n-amyl acetate, isoamyl acetate, methylisoamyl acetate, methoxybutyl acetate, sec-hexyl acetate, 2-ethylbutyl acetate, 2-ethylhexyl acetate, cyclohexyl acetate, methylcyclohexyl acetate, benzyl acetate, ethyl propionate, n-butyl propionate, isoamyl propionate, ethyl acetate, butyl stearate, butyl lactate, and amyl lactate; or aromatic carboxylic acid esters such as methyl salicylate, dimethyl phthalate and methyl benzoate.

According to one embodiment of the invention, the salt of amine compound in the reaction step may be contained in the solvent at a concentration of 20% by volume or less, for example, 1 to 20% by volume, or 5 to 20% by volume. When the concentration of the salt of amine compound contained in the solvent exceeds 20% by volume, a large amount of salt is likely to precipitate in the reaction step.

The reaction step may be progressed at a temperature of 165° C. or less, preferably 80° C. to 165° C.

According to one embodiment of the invention, when phosgene is dividedly charged in the reaction step, it can be charged in an amount of 10 to 30% by weight, or 12 to 30% by weight, or 15 to 28% by weight based on the entire amount of phosgene charged at a temperature of 80° C. to 100° C. or 85° C. to 95° C. Under such reaction conditions, rapid reactions are suppressed and an intermediate in the form of a carbamoyl-based salt can be selectively and effectively formed. Subsequently, while charging the remaining amount of phosgene at a temperature of 110° C. to 165° C. or 120° C. to 150° C., the intermediate and the phosgene can be reacted to obtain a reaction product containing an isocyanate compound.

The isocyanate compound may vary depending on the type of the amine compound used in the reaction step. For example, the isocyanate compound may be at least one compound selected from the group consisting of n-pentyl isocyanate, 6-methyl-2-heptane isocyanate, cyclopentyl isocyanate, hexamethylene diisocyanate (HDI), isophorone diisocyanate (IPDI), diisocyanatomethylcyclohexane (H6TDI), xylylene diisocyanate (XDI), diisocyanatocyclohexane (t-CHDI) and di(isocyanatocyclohexyl)methane (H12MDI).

In particular, the method for preparing an isocyanate compound according to an embodiment of the invention may be further useful for the preparation of xylylene diisocyanate (XDI). XDI includes 1,2-XDI (o-XDI), 1,3-XDI (m-XDI), and 1,4-XDI (p-XDI) as structural isomers.

The reaction step can be progressed either batchwise or continuously. The reaction step can be progressed in a reaction unit 100 that includes a reactor 110 having a rotating shaft; an amine compound salt supply line 10 and a phosgene supply line 20 that supply reactants to the inside of the reactor; a heat source that supplies a heat quantity to the reactor; and a reaction product transfer line 102 that transfers the reaction product obtained in the reactor to a subsequent purification step.

(Distillation Step)

Then, a distillation step is progressed in which the reaction product is distilled in a dividing-wall distillation column, thereby obtaining a stream containing the unreacted phosgene from the top of the dividing-wall distillation column, obtaining a stream containing the isocyanate compound from the bottom of the dividing-wall distillation column, and obtaining a stream containing the solvent from a side stream draw of the dividing-wall distillation column, FIG. 2(*a*) shows a sequence for separating compounds A, B and C in a conventional distillation column, and FIG. 2(*b*) shows the sequence for separating compounds A, B, and C in a dividing-wall distillation column. Here, the boiling points of the compounds A, B, and C are assumed to be A<B<C.

Referring to FIG. 2(*a*), in order to separate compounds A, B and C from a mixture of compounds A, B, and C through a conventional distillation process, a distillation column 1 for separating compound A from the mixture and a distillation column 2 for separating compounds B and C from the mixture of compounds B and C obtained from the distillation column 1 must be continuously arranged.

Meanwhile, referring to FIG. 2(*b*), the dividing-wall distillation column 30 has a structure in which a dividing wall 31 is placed inside to integrate a pre-fractionator side 33 and a main fractionator side (draw side) 35. In the dividing-wall distillation column 30, not only it is easy to operate by adjusting the pressure balance between the pre-fractionator side 33 and the draw side 35, but also the two distillation columns can be integrated and operated into one, thereby reducing cost burden and increasing energy efficiency.

If a feed, which is a mixture of compounds A, B and C, is supplied to the dividing-wall distillation column 30 shown in FIG. 2(*b*), in the pre-fractionator side 33, part of the compound B and A rise to a rectifying section 37, and the rest of compound B and C descends to a stripping section 39. In the rectifying section 37, compound A is discharged to the top of the dividing-wall distillation column 30. In the stripping section 39, compound C is discharged to the bottom of the dividing-wall distillation column 30. Then, compound B having a corresponding boiling point between compounds A and C is collected in the draw side 35 and discharged to the side stream draw of the dividing-wall distillation column 30.

According to one embodiment of the invention, in the distillation step, unreacted phosgene, an isocyanate compound as a main product, the solvent, hydrogen chloride as a by-product, and the like, which are contained in the reaction product, may be obtained by separating into the top, the bottom, and the side stream draw of the dividing-wall distillation column.

Among the components contained in the reaction product, unreacted phosgene can be obtained as a stream corresponding to compound A in FIG. 2(*b*), the isocyanate compound, which is the main product, can be obtained as a stream corresponding to compound C in FIG. 2(*b*), and the solvent may be obtained as a stream corresponding to compound B in FIG. 2(*c*).

Specifically, referring to FIGS. 1 and 2(*b*), the reaction product is supplied to the dividing-wall distillation column 210 through a reaction production transfer line 102. At the pre-fractionator side 33 of the dividing-wall distillation column 210, part of the solvent and phosgene rises to the rectifying section 37, and the rest of the solvent and the main product, isocyanate compounds, descends to the stripping section 39. The phosgene-enriched fraction in the rectifying section 37 is discharged to the column top stream line 293 connected to the top of the dividing-wall distillation column 210. In the stripping section 39, the isocyanate compound-enriched fraction is discharged to the bottom stream line 212 connected to the bottom of the dividing-wall distillation column 210. Then, the solvent-enriched fraction is collected in the draw side 35 and discharged to a side stream line 251 connected to the side stream draw of the dividing-wall distillation column 30.

In this manner, in the method for preparing an isocyanate compound according to an embodiment of the invention, phosgene and an isocyanate compound are separated from the reaction product by using a dividing-wall distillation column and, at the same time, the solvent can be obtained from a side stream draw of a dividing-wall distillation column. Thereby, a separate evaporator or process for removing the solvent is not required, and the process operation burden and energy consumption due to remixing of the solvent can be reduced.

Various factors affect the purity of materials discharged through the column top stream line 293, the bottom stream line 212, and the side stream line 251 in the dividing-wall distillation column 210 and the energy efficiency of the process. For example, the total number of column stages of the dividing-wall distillation column 210, the length of the dividing wall, the amount of reflux in the condenser 295, the amount of heat supplied in the reboiler 214, the vapor split ratio, the liquid split ratio, and the like can affect the purity of the discharged materials and the energy efficiency of the process. Since the distillation step according to the present invention requires a large amount of solvent, it is preferable from the viewpoint of energy reduction to conduct the distillation so that the liquid split ratio is 15% or less among the above factors.

That is, the distillation step may be progressed so that the liquid split ratio divided from the rectifying section 37 to the pre-separator side 33 of the dividing-wall distillation column is 15% or less. The liquid split ratio means the ratio of the liquid phase charged into the pre-fractionator side 33 to the total flow rate of the liquid phase descending from the rectifying section 37 of the dividing-wall distillation column. The liquid split ratio can be adjusted using a liquid distributor.

According to one embodiment of the invention, the stream containing unreacted phosgene discharged to the top of the dividing-wall distillation column 210 is transferred to a condenser 295 through a column top stream line 293. In the condenser 295, the gas phase containing phosgene is discharged through a gas phase discharge line 299, and the liquid is collected in the recovery drum 297, and then re-supplied to the upper part of the dividing-wall distillation column 210. Phosgene obtained through the gas phase discharge line 299 may be recycled as a reaction product of the reaction step.

At this time, in order to improve the distillation efficiency in the dividing-wall distillation column 210, the distillation step is preferably progressed so that the pressure at the top of the dividing-wall distillation column 210 is 20 torr or less. In one example, the distillation step is preferably progressed so that the pressure of the condenser 295 connected to the dividing-wall distillation column 210 is 20 torr or less. Preferably, the distillation step may be progressed so that the pressure of the condenser 295 connected to the dividing-wall distillation column 210 is 1 to 20 torr, 5 to 20 torr, or 10 to 20 torr.

According to one embodiment of the invention, the stream containing the isocyanate compound discharged to the bottom of the dividing-wall distillation column 210 is transferred to the reboiler 214 through the bottom stream line 212. In the reboiler 214, the low boiling fraction is re-supplied to the lower part of the dividing-wall distillation column 210, and the fraction containing the isocyanate compound is discharged through the isocyanate discharge line 219.

At this time, in order to improve the distillation efficiency in the dividing-wall distillation column 210, the distillation step is preferably progressed so that the temperature at the bottom of the dividing-wall distillation column is 165° C. or less. As an example, the distillation step is preferably progressed so that the temperature of the reboiler 214 connected to the dividing-wall distillation column 210 is 165° C. or less. Preferably, the distillation step may be progressed so that the temperature of the reboiler 214 connected to the distillation column 210 is 100° C. to 165° C., 120° C. to 165° C., or 130° C. to 160° C.

Further, in order to minimize the high temperature residence time of the reaction product in the distillation step, as the reboiler 214, apparatuses such as a kettle type reboiler, a thin-film evaporator, a force circulated reboiler, and a jacketed vessel type reboiler are preferably applied.

According to one embodiment of the invention, the solvent-containing stream discharged to the side stream draw of the dividing-wall distillation column 210 is transferred to a recovery drum 255 through the side stream line 251 and then the condenser 253. The solvent-containing stream collected in the recovery drum 255 is discharged through a solvent discharge line 259. Solvent obtained through the solvent discharge line 259 can be recycled to the reaction step.

The fraction containing the isocyanate compound discharged through the isocyanate discharge line 219 may include trace amounts of solvents, high boiling materials, and the like. If necessary, a step of purifying the fraction containing the isocyanate compound to obtain a high-purity isocyanate compound may be further progressed.

As a non-limiting example, a low boiling material-removing step may be progressed in which low boiling materials (i.e., lights) are removed from the fraction containing the isocyanate compound. In the low boiling material-removing step, the low boiling materials (lights) can be removed by a known low boiling material-removing unit from the fraction containing the isocyanate compound.

The low boiling material means a material having a boiling point lower than that of the isocyanate compound, which is the main product in the reaction step. Examples of the low boiling materials include materials produced by side reactions in the process of obtaining the main product. As an example, in the process of preparing XDI as the isocyanate compound, the low boiling material may include monoisocyanate such as (chloromethyl)benzyl isocyanate (CMBI) and ethylphenyl isocyanate (EBI).

According to one embodiment of the invention, in order to minimize the thermal denaturation of reaction products and the formation of by-products in the low boiling material-removing step, the low boiling material-removing step is preferably progressed at a temperature of 150° C. to 165° C. And, the low boiling material-removing step is preferably progressed under a pressure of 5 torr or less.

In one example, the low boiling material-removing step may be progressed under a distillation column, wherein setting the temperature at the bottom of the distillation column to 150° C. to 165° C. and operating the distillation column under a column top pressure of 5 torr or less can be advantageous to minimize the thermal degradation and the formation of by-products. Here, the temperature at the bottom of the distillation column may mean the temperature of a reboiler connected to the bottom of the distillation column.

Preferably, the temperature at which the low boiling material-removing step is progressed may be 150° C. to 165° C., or 155° C. to 165° C., or 155° C. to 162° C., or 160° C. to 162° C. And, preferably, the upper pressure at which the low boiling material-removing step is progressed may be 1 torr to 5 torr, or 2 torr to 5 torr, or 2 torr to 4 torr.

If the temperature and pressure at which the low boiling material-removing step is progressed do not satisfy the above ranges, the thermal denaturation and the formation of by-products in the low boiling material-removing step may increase, and the removal efficiency of low boiling materials may decrease, whereby the concentration of isocyanate compounds in the reaction product obtained from the low boiling material-removing step can be reduced.

In one example, the low boiling material-removing step can be progressed in a low boiling material-removing unit that includes a distillation column configured to remove low boiling materials from the isocyanate compound-containing fraction supplied through the isocyanate compound discharge line 219 of the distillation unit 200; a low boiling material discharge line that discharges low boiling materials to the top of the distillation column; and a reaction product transfer line that discharges the reaction product from which the low boiling materials have been removed to the bottom of the distillation column, and transfers it to a subsequent step.

In order to minimize the high temperature residence time of the reaction product in the low boiling material-removing step, a distillation column 440 equipped with apparatuses such as a kettle type reboiler, a thin-film evaporator, a force circulated reboiler, and a jacketed vessel type reboiler can be utilized.

As a non-limiting example, a high boiling material-removing step may be progressed in which high boiling materials (i.e., heavies) are removed from the reaction product from which the low boiling materials have been removed. In the high boiling material-removing step, high boiling materials (i.e., heavies) can be removed by a known high boiling material-removing unit from the reaction product from which the low boiling materials have been removed.

The high boiling material means a material having a boiling point higher than that of the isocyanate compound, which is the main product in the reaction step. Examples of the high boiling materials include high-molecular-weight by-products such as oligomers or polymers including dimers, trimers or higher multimers of isocyanate compounds formed in the step of obtaining the main product.

According to one embodiment of the invention, in order to minimize the thermal denaturation of the reaction product and the formation of by-products in the high boiling material-removing step, the high boiling material-removing step may preferably be progressed at a temperature of 145° C. to 165° C. and a pressure of 1 torr or less.

In one example, the high boiling material-removing step may be progressed under a thin-film evaporator, wherein setting the bottom temperature of the thin-film evaporator to 145° C. to 165° C. and operating the thin-film evaporator under an evaporator bottom pressure of 1 torr or less can be advantageous to minimize the thermal degradation and the formation of by-products.

Preferably, the temperature at which the high boiling material-removing step is progressed may be 145° C. to 165° C., or 150° C. to 165° C., or 150° C. to 160° C., or 155° C. to 160° C. And, preferably, the pressure at which the high boiling material-removing step is progressed may be 0.1 torr to 1 torr, or 0.5 torr to 1 torr.

If the temperature and pressure at which the high boiling material-removing step is progressed do not satisfy the above ranges, the thermal denaturation and the formation of by-products in the high boiling material-removing step may increase, and the removal efficiency of high boiling materials may decrease, whereby the concentration of the isocyanate compound obtained from the high boiling material-removing step may decrease.

In one example, the high boiling material-removing step may be progressed in a high boiling material-removing unit that includes a thin-film evaporator configured to remove high boiling materials from the reaction product supplied through the reaction product transfer line of the low boiling material-removing unit; an isocyanate compound discharge line that discharges an isocyanate compound to a condensing section of the thin-film evaporator; and a high boiling material discharge line that discharges the high boiling material to the bottom of the thin-film evaporator.

Advantageous Effects

According to the present invention, provided is a method for preparing an isocyanate compound that can increase energy efficiency while minimizing thermal denaturation of a reaction product and formation of by-products during the preparation of an isocyanate compound using phosgene.

BRIEF DESCRIPTION OF THE DRAWINGS

FIG. 1 schematically show the process and apparatus used in the method for preparing an isocyanate compound according to one embodiment of the present invention.

FIG. 2(*a*) shows a sequence for separating compounds A, B and C in a conventional distillation column, and FIG. 2(*b*) shows a sequence for separating compounds A, B and C in a dividing-wall distillation column.

DESCRIPTION OF REFERENCE NUMERALS

10: amine compound salt supply line
20: phosgene supply line
100: reaction unit
110: reactor
102: reaction product transfer line
200: distillation unit
210: dividing-wall distillation column
212: bottom stream line
214: reboiler
219: isocyanate compound discharge line
251: side stream line
253: condenser
255: recovery drum
259: solvent discharge line
293 column top stream line
295 condenser
297: recovery drum
299: gas phase discharge line
A, B, C: compound
1, 2: distillation column
30: dividing-wall distillation column
31: dividing wall
33: pre-fractionator side
35: main fractionator side (draw side)
37: rectifying section
39: stripping section

DETAILED DESCRIPTION OF THE EMBODIMENTS

Hereinafter, the actions and effects of the invention will be explained in more detail through specific examples of the invention. However, these examples are presented only as the illustrations of the invention, and the scope of the right of the invention is not determined thereby.

Example 1

1,3-XDI (m-XDI) was prepared by the following process using the apparatus shown in FIG. 1.

(Reaction Step)

Under normal temperature and pressure conditions, 500 kg of hydrochloric acid and 560 kg of m-xylylenediamine (m-XDA) were reacted in 6500 kg of 1,2-dichlorobenzene (o-DCB) solvent for 4 hours to form 870 kg of the hydrochloride salt of m-xylylenediamine.

870 kg of the hydrochloride salt of m-xylylenediamine was charged into a reactor 110 through a supply line 10, and the temperature of the reactor was raised to 125° C. During the progress of the reaction, a total of 1359 kg of phosgene was put into the reactor through the supply line 20, and stirred. A dry ice-acetone condenser was used from the time of charging phosgene to the time of completion of the reaction to prevent phosgene from leaking to the outside. The reaction was allowed to progress for 1.5 hours at a temperature of 90° C.

After that, the internal temperature of the reactor was heated to 125° C., and 6000 kg of phosgene was further charged. The temperature of the reactor was maintained at 125° C., and further stirred for 4.5 hours until the reaction solution became clear. Heating was stopped after the reaction solution became clear. The reaction product obtained by the above method was transferred to the distillation unit 200 through a transfer line 102.

(Distillation Step)

The dividing-wall distillation column 210 of the distillation unit 200 was configured such that a stream containing unreacted phosgene from the reaction product supplied through the transfer line 102 was obtained from the top of the dividing-wall distillation column, a stream containing 1,3-XDI was obtained from the bottom of the dividing-wall distillation column, and a stream containing the solvent was obtained from a side stream draw of the dividing-wall distillation column.

Specifically, the dividing-wall distillation column 210 is composed of a dividing-wall located at the center of the column, a liquid distributor, a packing support, a grid, and the like. The pre-fractionator side, the main fractionator side, the rectifying section, and the stripping section were packed with Mellapak, which is a kind of structural packing.

Total number of columns: 20 vapor split ratio=50:50 liquid split ratio=10:90

In the distillation step, the pressure of the condenser 295 connected to the dividing-wall distillation column 210 was set to 15 torr, and the temperature of the reboiler 214 connected to the dividing-wall distillation column 210 was set to 160° C.

About 1350 kg/hr of the reflux stream from the top of the dividing-wall distillation column 210 was re-charged into the dividing-wall distillation column 210, which corresponds to a reflux ratio of about 39.5 relative to the column top outflow amount.

The gas phase containing phosgene in the condenser 295 was discharged through a gas phase discharge line 299, and the liquid was collected in a recovery drum 297, and then re-supplied to the top of the dividing-wall distillation column 210. The phosgene obtained through the gas phase discharge line 299 was recycled as a reactant of the reaction step.

The low boiling fraction in the reboiler 214 was re-supplied to the lower part of the dividing-wall distillation column 210, and the fraction containing 1,3-XDI was discharged through an isocyanate discharge line 219.

The solvent-containing stream discharged to the side stream draw of the dividing-wall distillation column 210 was transferred to the recovery drum 255 through the side stream line 251 and then the condenser 253. The solvent-containing stream collected in the recovery drum 255 was discharged through a solvent discharge line 259. Solvent obtained through a solvent discharge line 259 was recycled to the reaction step.

Example 2

An isocyanate compound including 1,3-XDI (m-XDI) was obtained in the same manner as in Example 1, except that in the distillation step, the dividing-wall distillation column 210 was operated so that the pressure of the condenser 295 connected thereto was 5 torr.

Example 3

An isocyanate compound including 1,3-XDI (m-XDI) was obtained in the same manner as in Example 1, except that in the distillation step, the dividing-wall distillation column 210 was operated so that the temperature of the reboiler 214 connected thereto was 120° C.

Comparative Example 1

1,3-XDI (m-XDI) was prepared by the following process using the apparatus shown in FIG. 2(*a*).

(Reaction Step)

A reaction product was prepared in the same manner as in Example 1. The reaction product was supplied to a first distillation column 1 through a transfer line.

(First Distillation Step)

The first distillation column 1 was configured so as to be able to remove a gas phase including phosgene from the reaction product supplied through the transfer line.

Specifically, the first distillation column 1 used was a packing tower packed with Mellapak, which is a type of structural packing, and had a height of about 6 m.

The temperature at the bottom of the first distillation column 1 was set to 155° C., and the first distillation column 1 was operated under a column top pressure of 400 torr.

About 150 kg/hr of the reflux stream was re-charged to the first distillation column 1, which corresponds to a reflux ratio of about 3.2 relative to the column top outflow amount.

A gas phase including phosgene was discharged through a gas phase discharge line connected to the top of the first distillation column 1. The reaction product from which the gas phase was removed was transferred to the next process through a transfer line connected to the bottom of the first distillation column 1.

(Second Distillation Step)

The second distillation column 2 was configured so as to be able to remove the solvent from the reaction product supplied through the transfer line.

Specifically, the second distillation column 2 used was a packing tower paced with Mellapak, which is a type of structural packing, and had a height of about 7 m.

The temperature at the bottom of the second distillation column 2 was set to 160° C. and the second distillation column 2 was operated under a column top pressure of 15 torr.

About 600 kg/hr of the reflux stream was re-charged to the second distillation column 2, which corresponds to a reflux ratio of about 0.5 to the column top outflow amount.

A solvent including 1,2-dichlorobenzene (o-DCB) was discharged through a solvent discharge line connected to the top of the second distillation column 2. The reaction product from which the solvent was removed was discharged through a transfer line connected to the bottom of the second distillation column 2.

Comparative Example 2

An isocyanate compound including 1,3-XDI (m-XDI) was obtained in the same manner as in Example 1, except that in the distillation step, the dividing-wall distillation column 210 was operated so that the pressure of the condenser 295 connected thereto was 30 torr.

Comparative Example 3

An isocyanate compound including 1,3-XDI (m-XDI) was obtained in the same manner as in Example 1, except that in the distillation step, the dividing-wall distillation column 210 was operated so that the temperature of the reboiler 214 connected thereto was 170° C.

Test Example

Part of the fraction obtained from each outlet of Examples and Comparative Examples was recovered, and subjected to gel permeation chromatography analysis. The contents of the main components identified through the above analysis are shown in Tables 1 to 6 below.

In addition, the energy per unit time (kcal/hr) charged to the performance of the process according to Examples and Comparative Examples was measured, and shown in Tables 1 to 6 below.

In Tables 1 to 6 below, "Heavies" means the fraction containing m-XDI obtained through the isocyanate compound discharge line 219.

TABLE 1

| | Example 1 | | |
|---|---|---|---|
| | Colum top stream | Side stream | Colum bottom stream |
| HCl (wt %) | 0.4 | — | — |
| Phosgene (wt %) | 99.5 | — | — |
| oDCB (wt %) | 0.1 | 100 | 7.1 |
| Heavies (wt %) | — | — | 92.9 |
| Energy (kcal/hr) | | 283,000 | |

TABLE 2

| | Example 2 | | |
|---|---|---|---|
| | Colum top stream | Side stream | Colum bottom stream |
| HCl (wt %) | 0.5 | — | — |
| Phosgene (wt %) | 97.8 | — | — |
| oDCB (wt %) | 1.7 | 100 | 4.1 |
| Heavies (wt %) | — | — | 95.9 |
| Energy (kcal/hr) | | 275,000 | |

TABLE 3

| | Example 3 | | |
|---|---|---|---|
| | Colum top stream | Side stream | Colum bottom stream |
| HCl (wt %) | 0.4 | — | — |
| Phosgene (wt %) | 99.5 | — | — |
| oDCB (wt %) | 0.1 | 100 | 18.3 |
| Heavies (wt %) | — | — | 81.7 |
| Energy (kcal/hr) | | 261,000 | |

TABLE 4

| | Comparative Example 1 | | |
|---|---|---|---|
| | Top of the first distillation column | Top of the second distillation column | Top of the second distillation column |
| HCl (wt %) | 0.4 | — | — |
| Phosgene (wt %) | 99.4 | — | — |
| oDCB (wt %) | 0.2 | 100 | 3.0 |
| Heavys (wt %) | — | — | 97.0 |
| Energy (kcal/hr) | | 363,000 | |

TABLE 5

| | Comparative Example 2 | | |
|---|---|---|---|
| | Colum top stream | Side stream | Colum bottom stream |
| HCl (wt %) | 0.5 | — | — |
| Phosgene (wt %) | 99.2 | — | — |
| oDCB (wt %) | 2.6 | 100 | 12.1 |
| Heavies (wt %) | — | — | 87.9 |
| Energy (kcal/hr) | | 307,000 | |

TABLE 6

| | Comparative Example 3 | | |
|---|---|---|---|
| | Colum top stream | Side stream | Colum bottom stream |
| HCl (wt %) | 0.4 | — | — |
| Phosgene (wt %) | 99.5 | — | — |
| oDCB (wt %) | 0.1 | 100 | 3.7 |
| Heavies (wt %) | — | — | 94.3 |
| Energy (kcal/hr) | | 411,000 | |

Referring to Tables 1 to 6, it was confirmed that the method for preparing an isocyanate compound according to Examples can increase energy efficiency while obtaining a high-purity isocyanate compound.

On the contrary, it was confirmed that in Comparative Examples, the thermal denaturation and by-product formation increased, and the concentration and energy efficiency of the final isocyanate compound were low.

The invention claimed is:

1. A method for preparing an isocyanate compound, comprising:

a reaction step of reacting a salt of amine compound with phosgene in the presence of a solvent to obtain a reaction product containing an isocyanate compound, the solvent and unreacted phosgene, and a distillation step of distilling the reaction product in a dividing-wall distillation column, so that a stream containing the unreacted phosgene is obtained from the top of the dividing-wall distillation column, a stream containing the isocyanate compound is obtained from the bottom of the dividing-wall distillation column, and a stream containing the solvent is obtained from a side stream draw of the dividing-wall distillation column, wherein the distillation step is progressed so that the pressure at the top of the dividing-wall distillation column is 5 torr to 20 torr.

wherein the distillation step is progressed so that the temperature at the bottom of the dividing-wall distillation column is 165° C. or less and the temperature of a reboiler connected to the dividing-wall distillation column is 120° C. to 165° C.

2. The method of claim 1, wherein the distillation step is progressed so that, of a total flow volume of liquid descending from the rectifying section of the dividing-wall distillation column, a flow volume of a portion introduced into a pre-fractionator side of the dividing-wall distillation column is 15% or less.

3. The method of claim 1, wherein the amine compound is an aliphatic amine having an aliphatic group in its molecule.

4. The method of claim 1, wherein the amine compound is at least one alicyclic diamine selected from the group consisting of bis(aminomethyl)cyclohexane, dicyclohexylmethanediamine, cyclohexanediamine, methylcyclohexanediamine, dicyclohexyldimethylmethanediamine, and 2,2-dimethyldicyclohexylmethanediamine.

5. The method of claim 1, wherein the amine compound is at least one sulfur-containing aliphatic amine selected from the group consisting of bis(aminomethyl)sulfide, bis(aminoethyl)sulfide, bis(aminopropyl)sulfide, bis(aminohexyl)sulfide, bis(aminomethyl) sulfone, bis(aminomethyl) disulfide, bis(aminoethyl)disulfide, bis(aminopropyl) disulfide, bis(aminomethylthio)methane, bis(aminoethylthio)methane, bis(aminoethylthio)ethane, and bis(aminomethylthio)ethane.

6. The method of claim 1, wherein the amine compound is at least one aromatic xylylene diamine selected from the group consisting of m-xylylenediamine, p-xylylenediamine and o-xylylenediamine.

7. The method of claim 1, wherein the salt of amine compound is a hydrochloride or carbonic acid salt of the amine compound.

8. The method of claim 1, wherein the reaction step is progressed in the presence of a solvent containing at least one of an aromatic hydrocarbon-based solvent and an ester-based solvent.

9. The method of claim 8, wherein the solvent is at least one compound selected from the group consisting of monochlorobenzene, 1,2-dichlorobenzene, and 1,2,4-trichlorobenzene.

10. The method of claim 1, further comprising a low boiling material-removing step of removing low boiling materials having a boiling point lower than that of the isocyanate compound from a steam containing an isocyanate compound.

11. The method of claim 1, further comprising a high boiling material-removing step of removing high boiling materials having a boiling point higher than that of the isocyanate compound from a steam containing an isocyanate compound.

* * * * *